United States Patent
Nair et al.

(10) Patent No.: US 6,656,914 B2
(45) Date of Patent: *Dec. 2, 2003

(54) METHOD FOR TREATING TUMORS CAUSED BY APC GENE MUTATION WITH ANTHOCYANINS AND CYANIDIN

(75) Inventors: Muraleedharan G. Nair, Okemos, MI (US); Leslie D. Bourquin, Lansing, MI (US); Navindra P. Seeram, East Lansing, MI (US); Soo-Young Kang, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/776,527

(22) Filed: Feb. 2, 2001

(65) Prior Publication Data

US 2001/0016573 A1 Aug. 23, 2001

Related U.S. Application Data

(63) Continuation of application No. 09/494,077, filed on Jan. 28, 2000, now abandoned.

(51) Int. Cl.[7] .................. A01N 43/04; A61K 35/78; C07H 1/00; C07H 15/00; C07H 17/00
(52) U.S. Cl. .................. 514/28; 514/27; 424/735; 424/777; 424/725; 536/8; 536/1
(58) Field of Search .................. 424/195.1, 725, 424/735, 777; 426/541, 544; 435/195; 536/1, 8; 514/27, 28

(56) References Cited

U.S. PATENT DOCUMENTS 4,297,220 A  10/1981  Meitzner et al.
5,985,636 A  11/1999  Gray et al.

OTHER PUBLICATIONS

Kamei et al. Influence of OH Group and Sugar Bonded to Flavonoids on Flavonoid–Mediated Supression of Tumor Growth In Vitro; Cancer Biotherapy & Radiopharmaceuticals, vol. 11, No. 4 (1996), pp. 247–249.*
American Cancer Society, Cancer Facts and Figures (1997).
Doll and Peto, J. Natl. Cancer Inst. 66:1192–1308 (1981).
Stavric, B., Clin Biochem 27:319–332 (1994).
Wang, H., et al., J. Nat Prod 62:86–88 (1999).
Moser, A.R., et al., Science 247:322–324 (1990).
Su, L.K., et al., Science 256:668–670 (1992).
Boolbol, S.K., et al., Cancer Res. 56:2556–2560 (1996).
Jacoby, R.F., et al., Cancer Res. 56:710–714 (1996).
Wang, et al., J. Agric. Food Chem. 45:2556–2560 (1997).
Chiu, C.–H., et al., Cancer Res. 57:4267–4273 (1997).
Li, K.C., et al., J. Am. Chem. Soc. 78:979–980.
Harbone, J.B., et al., Phytochemistry 3:453–463 (1964).
Dekazos, E. D., J. Food Sci. 35:237–241 (1970).
Chandra, A., et al., J. Agric. Food Chem 40:967 969 (1992).
Shrikhande, A.J. and F.J. Francis, J. Food Sci. 38:649–651 (1973).
Chandra, A. et al., J. Agric. Food Chem. 41:1062 (1993).
Arora, A. and G.M. Strasburg, J. Amer. Oil Chem. Soc. 74:1031–1040 (1997).
Mahmoud, N.N., et al. Carcinogenesis 19:87–91 (1998).

* cited by examiner

*Primary Examiner*—Jon P. Weber
*Assistant Examiner*—Patricia Patten
(74) *Attorney, Agent, or Firm*—Ian C. McLeod

(57) ABSTRACT

A method for inhibiting a tumor in a mammal using a composition comprising an anthocyanin or cyanidin from a berry is described. The method involves using the composition in an amount and for a time to inhibit the tumor. The composition can include other antitumor agents.

23 Claims, 4 Drawing Sheets

| | $R_1$ | $R_2$ |
|---|---|---|
| Anthocyanin 1 (cyanidin-3-glucosylrutinoside) |  |  |
| Anthocyanin 2 (cyanidin-3-rutinoside) | H |  |
| Anthocyanin 3 (cyanidin-3-glucoside) | H | H |

| Compound | $R_1$ | $R_2$ | $R_3$ | $R_4$ | $R_5$ | $R_6$ | $R_7$ |
|---|---|---|---|---|---|---|---|
| Quercetin | OH | OH | OH | OH | H | OH | H |
| Kaempferol | OH | H | OH | OH | H | OH | H |
| Luteolin | OH | OH | H | OH | H | OH | H |
| Quercetrin | OH | OH | rhamnose | OH | H | OH | H |
| Kaempferol 3-rutinoside | OH | H | rutinose | OH | H | OH | H |
| 3'-methoxy kaempferol 3-rutinoside | OH | OMe | rutinose | OH | H | OH | H |
| 5,8,4'-trihydroxyl-6,7-dimethoxyflavone | OH | H | H | OH | OMe | OH | OMe |

| Compound | $R_1$ | $R_2$ | $R_3$ |
|---|---|---|---|
| Genistein | OH | OH | OH |
| Genistin | OH | OH | glucose |
| Biochanin A | OMe | OH | OH |
| Daidzein | OH | H | OH |
| Formononetin | OMe | H | OH |

METHOD FOR TREATING TUMORS CAUSED BY APC GENE MUTATION WITH ANTHOCYANINS AND CYANIDIN

CROSS-REFERENCE TO RELATED APPLICATION

This application is a continuation of application Ser. No. 09/494,077, filed Jan. 23, 2000, now abandoned.

BACKGROUND OF THE INVENTION (1) Field of the Invention

The present invention relates to a method for inhibiting a tumor particularly by feeding a mammal a composition comprising anthocyanins. In particular, the compositions of anthocyanins inhibit intestinal adenomas.

(2) Description of Related Art

Tumors occur in mammals and can be life threatening. In humans this can include prostate, colon, breast, lung, and kidney, prostate, liver, lymphoma/CNS, leukemia, pancreatic, gastric, esophageal, ovarian, uterine and testicular tumors, for instance.

Colon cancer is the second most common cause of cancer mortality and the fourth most common in incidence in the United States (American Cancer Society, Cancer Facts and Figures 1997). Diet has been considered to account for 30% of incidence of colon cancer (Doll and Peto, J. Natl Cancer Inst 66:1192–1308 (1981)). Epidemiological studies have shown consuming fruits and vegetables lowers incidences of various cancers including colon cancer. This anticancer effect of fruits and vegetables is thought to be due in part to antioxidant effects of phytochemicals (Stavric, B., Clin Biochem 27:319–332 (1994)). Other potential anticancer mechanisms are inhibition of carcinogen formation, blocking biotransforming enzyme actions, inducing oxidative detoxification, and trapping and scavenging electrophilic agents (Stavric, B., Clin Biochem 27:319–332 (1994)).

Tart cherries contain various phytochemicals including anthocyanins and cyanidin. Anthocyanins are flavonoid pigments in many fruits and vegetables as well as cherries. Cyanidin is the major aglycone in cherries and its glycosylated form provides the anthocyanins. All anthocyanins are derivatives of the basic flavylium cation structure. Montmorency and Balaton cherries contain 120 and 220 mg/g, respectively, of anthocyanins (Wang, H., et al, J. Nat Prod 62:86–88 (1999)). These anthocyanins have been found to be antioxidants of lipids, particularly in foods as described in U.S. Pat. No. 5,985,636 to Gray et al., and inhibit cyclooxygenase enzymes as described in U.S. application Ser. No. 09/337,313, filed Jun. 21, 1999. In this study, cyanidin was intermediate in efficacy between aspirin and the non-steroidal anti-inflammatory drug, flurbiprofen. The anthocyanins are labile to heating and drying destroys their effectiveness.

The Min mouse has been proposed to be a model for the study of human colorectal cancer (Moser, A. R., et al, Science 247:322–324 (1990)). A mutant mouse lineage predisposed to multiple intestinal neoplasia (Min) results from a mutation in the murine homolog of the adenomatous polyposis coli (APC) gene (Su, L. K., et al, science 256:668–670 (1992)). The APC gene is also mutated in humans who develop sporadic colon cancer as well as persons with familial adenomatosis polyposis (FAP), an autosomal dominantly inherited disease that predisposes to colorectal cancer. The primary phenotype of mice carrying this mutation appears to be the development of multiple adenomas, which progress to adenocarcinomas of the intestine in older mice. Min is transmitted by affected mice to 50% of progeny with an unbiased sex distribution, as is characteristic of a fully penetrant autosomal dominant trait (Moser, A. R., et al, Science 247:322–324 (1990)). The Min mouse strain is an excellent animal model for the anticarcinogenic potential of dietary factors and other potential cancer therapeutic agents (e.g. NSAIDS).

Non-steroidal anti-inflammatory drugs (NSAIDs) that inhibit cyclooxygenase (COX) enzymes have been found to possess preventive effects for colon cancer. Research on the NSAIDs sulindac and proxicam in Min mice showed that they reduced the incidence of intestinal tumors (Boolbol, S. K., et al, Cancer Res. 56:2556–2560 (1996); Jacoby, R. F., et al, Cancer Res. 56:710–714 (1996)).

There is a need for a method of treatment which does not involve NSAIDS and is based upon a phytoceutical.

SUMMARY OF THE INVENTION

The present invention relates to a method for inhibiting a tumor which comprises: providing a composition comprising an anthocyanin from a berry or cyanidin in contact with the tumor over a period of time sufficient to inhibit the tumor.

The inhibition can be in vivo or in vitro. The compositions can contain bioflavonoids and phenolics naturally present in the berry.

The present invention also relates to a method for inhibiting a tumor in a mammal which comprises: feeding the mammal a composition comprising an anthocyanin from a berry or cyanidin in an amount and for a period of time sufficient to inhibit the tumor.

Further, the present invention relates to a method for inhibiting intestinal adenomas in a mammal which comprises: feeding the mammal a composition comprising an anthocyanin from cherries or cyanidin in an amount and for a period of time sufficient to inhibit the intestinal adenomas.

Anthocyanins are flavonoid pigments in blue and red fruits and vegetables including cherries. Cyanidin is the primary aglycone form of tart cherry anthocyanin. The dosage amount is preferably between about 0.1 and 300 mg per day per kg of body weight of the mammal.

Preferably the anthocyanins are between about 70% to 100% by weight of the composition, with the balance, if present, being the phenolics and the bioflavonoids. U.S. Pat. No. 5,985,636 to Gray et al describes the isolation of the anthocyanins in detail.

The compositions of the present invention can be combined with other active agents which have antitumor properties to provide greater effectiveness. These include NSAIDS.

The term "inhibiting" means preventing the formation of the tumor and/or causing the tumor to shrink. The term "tumor" includes carcinomas, sarcomas and lymphoid tumors.

The compounds of the present invention can be applied topically or can be fed orally depending upon the type of tumor. Enteral administration can be via nasogastric tube or percutaneous enterogastrostomy (PEG). Parenteral administration can be by administration (peripheral or central). They can also be injected into the tumor. In each instance a suitable carrier and an adjuvant is included where necessary.

The term "anthocyanins" means the compounds that impart color in berries.

The term "bioflavonoids" means the isoflavonoids and flavonoid compounds contained in berries.

The term "phenolics" refers to compounds with a phenyl group and having one or more hydroxyl groups from berries.

OBJECTS

It is therefore an object of the present invention to provide a natural source berry composition which can be used as an antitumor agent. It is further an object of the present invention to provide naturally a occurring phytoceutical which is inexpensive to prepare. These and other objects will become increasingly apparent by reference to the following description and the drawings.

DESCRIPTION OF PREFERRED EMBODIMENTS

Figure 1:
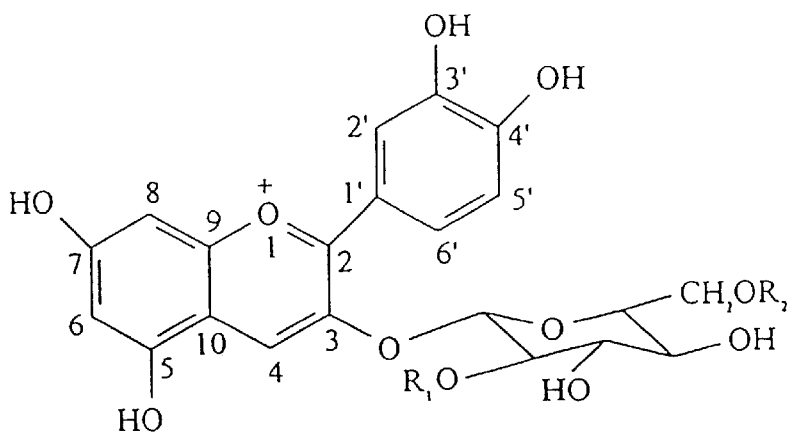
FIG. 1 shows the structure of select anthocyanins (colorants) that have been isolated from BALATON and MONTMORENCY cherries. The aglycone cyanidin has a hydroxyl group at position 3.
Figure 1:
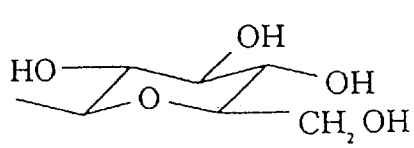
Figure 1:
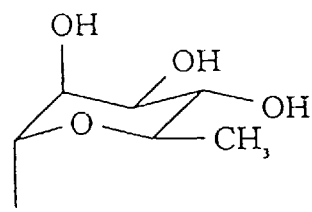
Figure 1:
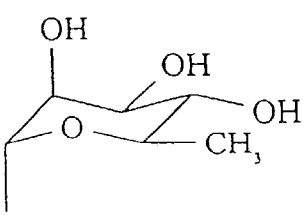

A preferred method for producing a mixture comprising anthocyanins, bioflavonoids and phenolics from berries as a composition comprises providing an aqueous solution containing the anthocyanins, bioflavonoids and phenolics from the berries; removing the anthocyanins, bioflavonoids and phenolics onto a resin surface from the aqueous solution; eluting the resin surface with an eluant to remove the anthocyanins, bioflavonoids and phenolics from the resin surface; and separating the eluant from the anthocyanins, bioflavonoids and phenolics.

In particular, a preferred method for producing anthocyanins, bioflavonoids and phenolics from berries as a composition comprises providing a first batch of berries, wherein the berries are fresh or quick frozen and thawed; disrupting the berries and separating pulp from the juice; extracting the anthocyanins, bioflavonoids and phenolics from the pulp into an aqueous solution; removing the anthocyanins, bioflavonoids and phenolics onto adsorbent resin particles from the aqueous solution containing the anthocyanins, bioflavonoids and phenolics separated from the pulp; washing the resin particles with a lower alkanol to remove the anthocyanins, bioflavonoids and phenolics from the resin particles; separating the alkanol from the anthocyanins, the bioflavonoids and phenolics and repeating the above steps with the separated alkanol and the resin particles from which the anthocyanins, bioflavonoids and phenolics have been removed with a second batch of the berries. The preferred method uses cherries.

Further, a preferred consumable composition for use in the method comprises in admixture: dried mixture of isolated anthocyanins, bioflavonoids and phenolics from berries; and a food grade carrier, wherein the weight ratio of the mixture to the carrier is between about 0.1 to 100 and 100 to 0.1.

Finally, a preferred method is provided for inhibiting tumors in a mammal which comprises feeding the mammal a consumable composition which comprises in admixture: dried mixture of isolated anthocyanins, bioflavonoids and phenolics removed from berries; and a food grade carrier wherein the weight ratio of the mixture to the carrier is between about 0.1 to 100 and 100 to 0.1. It is preferred that the composition contain at least in part dried berry pulp.

The preferred cherries used in the present invention can be sweet or sour (tart). Sour cherries contain high levels of malic acid in addition to other organic acids which contributes to the sour taste of tart cherries. The method isolates malic acid and other organic acids containing sugars, which can be used in foods to provide tartness and flavor. Most preferred are the BALATON and MONTMORENCY cherries.

The isolated mixture of anthocyanins, bioflavonoids and phenolics can be used as a natural nutraceutical/dietary supplement. In this regard, the isolated mixture may be provided in a powdered, liquid, or solid form. For example, the mixture may be in a reconstitutable powder composition that, when reconstituted with, for example, water, milk or some other similar liquid will provide a drink. Alternatively, the mixture may be in a solid form such as tablets, gel caps, soft gels, and the like. In addition, the mixture may be incorporated into foodstuffs. In general, a mixture may be provided in a form such that the anthocyanins, bioflavonoids and phenolics are present in an amount in the range from about 0.01% to about 50%, preferably from about 0.1% to about 30%, more preferably, from about 0.5% to about 25%, by weight of the total composition.

As an example, when the mixtures are provided in the form of a tablet, the tablet may provide a daily dose of the anthocyanins and bioflavonoids of about 0.1 mg to 300 mg, desirably from 1 to 200 mg, preferably a daily dose of 60–100 mg. It is noted that one hundred (100) cherries provide 60 to 100 mg of anthocyanins. The phenolics (FIG. 4) may be provided in an amount of 0.1 to 50 mg as a daily dose. One hundred cherries provide 1–50 mg of phenolics. The amount of the anthocyanins, bioflavonoids and phenolics can be adjusted by isolating the individual compounds and blending them together. In one embodiment, a natural mixture of the anthocyanins, bioflavonoids and phenolics may be used. The composition can also be provided in liquid form with equivalent dosages.

The resin has a surface to which the anthocyanins, bioflavonoids and the phenolics are adsorbed. A preferred class of adsorptive resins are polymeric crosslinked resins composed, of styrene and divinylbenzene such as, for example, the AMBERLITE series of resins, e.g., AMBERLITE XAD-4 and AMBERLITE XAD-16, which are available commercially from Rohm & Haas Co., Philadelphia, Pa. Other polymeric crosslinked styrene and divinylbenzene adsorptive resins suitable for use according to the invention are XFS-4257, XFS-4022, XUS-40323 and XUS-40322 manufactured by The Dow Chemical Company, Midland, Mich., and the like.

It is preferred to use commercially available, government-approved (where required), styrene-divinyl-benzene (SDVB) cross-linked copolymer resin, (e.g., AMBERLITE XAD-16). Thus, in the preferred embodiment, AMBERLITE XAD-16, commercially available from Rohm and Haas Company, and described in U.S. Pat. No. 4,297,220, is used as the resin. This resin is a non-ionic hydrophobic, cross-linked polystyrene divinyl benzene adsorbent resin. AMBERLITE XAD-16 has a macroreticular structure, with both a continuous polymer phase and a continuous pore phase. In a particularly preferred embodiment, the resin used in the present invention has a particle size ranging from 100–200 microns.

It is contemplated that other adsorbents such as those in the AMBERLITE XAD adsorbent series, which contain hydrophobic macroreticular resin beads, with particle sizes in the range of 100–200 microns, will also be effective in the methods of the present invention. Moreover, different variations of the AMBERLITES, such as the AMERCHRON CG series of adsorbents, used with particle sizes in the range of 100–200 microns, may also be suitable for use, in the present invention. The AMBERLITE XAD-16 is preferred since it can be re-used many times (over 100 times). However, it is contemplated that for food, the use of governmentally-approved resins in the present invention will be considered important and/or desirable.

Any solvent can be used to remove the adsorbed anthocyanins, bioflavonoids and phenolics. Preferred are lower alkanols containing 1 to 4 carbon atoms and most preferred is ethanol (ethyl alcohol) since it is approved for food use. Typically the ethanol is azeotroped with water; however, absolute ethanol can be used. Water containing malic acid and sugars in the cherries pass through the column. These are collected and can be used in foods as flavors.

The anthocyanins, bioflavonoids and phenolics are preferably isolated from the BALATON and the MONTMORENCY cherries. The composition of the cherries is in part shown in part by U.S. application Ser. No. 08/799,788 filed Feb. 12, 1997 and in part U.S. application Ser. No. 60/111,945, filed Dec. 11, 1998. As described in these applications, the Montmorency (*Prunus cerasus*) variety constitutes more than 95% of tart cherry cultivations in Michigan and USA. However, Balaton tart cherry (*P. cerasus*), a new tart cherry cultivar, is being planted to replace Montmorency in several Michigan orchards. This cherry has higher anthocyanin contents and is regarded as a better variety. Anthocyanin contents of Montmorency and Balaton tart cherries have been reported (Wang, et al., 1997; Chandra et al., 1993). However, a detailed investigation of other phenolic compounds in Balaton tart cherry was not carried out before. Early studies have shown that MONTMORENCY cherry contains cyanidin-3-gentiobioside and cyanidin-3-rutinoside (Li, K. C., et al., J. Am. Chem. Soc. 78:979–980 (1956)). Cyanidin-3-glucosylrutinoside was also found in six out of the seven sour cherry varieties (Harbone, J. B., et al., Phytochemistry 3:453–463 (1964)). Dekazos (Dekazos, E. D., J. Food Sci. 35:237–241 (1970)) reported anthocyanin pigments in MONTMORENCY cherry as peonidin-3-rutinoside, peonidin and cyanidin along with cyanidin-3-sophoroside, cyanidin-3-rutinoside and cyanidin-3-glucoside. However, cyanidin-3-glucosylrutinoside as well as cyanidin-3-glucoside, cyanidin-3-sophoroside and cyanidin-3-rutinoside were identified as main pigments in sour cherries. Using HPLC retention values, Chandra et al (Chandra, A., et al., J. Agric. Food Chem 40:967–969 (1992)) reported that cyanidin-3-sophoroside and cyanidin-3-glucoside were the major and minor anthocyanins, respectively, in Michigan grown MONTMORENCY cherry. Similarly, cyanidin-3-xylosylrutinoside was detected as a minor pigment in MONTMORENCY cherry (Shrikhande, A. J. and F. J. Francis, J. Food Sci. 38:649–651 (1973)).

The term "carrier" or "bulking agent" is used to mean a composition, which is added to increase the volume of the composition of the purified composition from the cherry. Preferred is dried cherry pulp. The bulking agent can include any edible starch containing material, protein, such as non-fat dry milk. Within this group are flour, sugar, soybean meal, maltodextrin and various condiments, such as salt, pepper, spices and herbs, for instance. The bulking agent is used in an amount between about $10^{-6}$ and $10^{6}$ parts by weight of the mixture.

The composition is introduced into the food in an amount between about 0.1 and 300 mg/gm of the active ingredients per gram of the food. The amount is preferably selected so as to not affect the taste of the food and to produce the most beneficial result. The food can be high (wet) or low moisture (dry) as is well known to those skilled in the art. When used as a dietary supplement the tablets contain between 0.1 to 1 gram of active ingredient. A particular food is cooked meat and other prepared foods where the composition provide antioxidant properties to the food and optionally color. The composition can be dispensed as a condiment on the prepared food.

Figure 2:
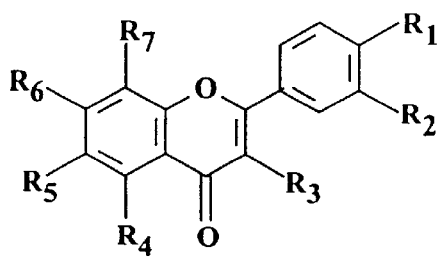
FIGS. 2 and 3 are drawings showing the major bioflavonoids isolated from the cherries.
Figure 3:
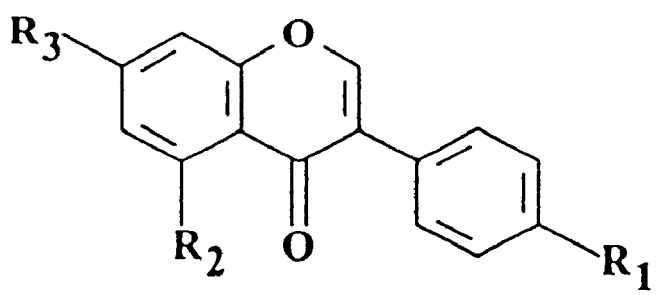

Methods have been developed for extraction and isolation of phytochemicals (Chandra, A. et al., J. Agric. Food Chem. 41:1062 (1992); Wang, H., et al., J. Agric. Food Chem. 45:2556–2560 (1997)) and for rapid screening of antioxidant activity (Arora, A. and G. M. Strasburg, J. Amer. Oil Chem. Soc. 74:1031–1040 (1997)). These methods are being utilized to identify and characterize the antioxidant compounds from BALATON and MONTMORENCY cherries. Juiced cherry tissue was sequentially extracted with hexane, ethyl acetate and methanol. Both methanol and ethyl acetate fractions showed strong antioxidant activity in the screening assay. The ethyl acetate fraction was further purified by silica gel vacuum liquid chromatography to yield four subfractions; the subfraction which showed the strongest antioxidant activity was further separated into seven fractions by preparative reverse phase HPLC. FIGS. 2 and 3 show the bioflavonoids isolated from the BALATON cherries. There are thus numerous analogous or homologous compounds in the tart cherries.

Two novel phenolic compounds were identified:
I) 1-(3'-4'-dihydroxy cinnamoyl)-2,3-dihydroxy cyclopentane, and
II) 1-3'-4'-dihydroxy cinnamoyl)-2,5-dihydroxy cyclopentane.

Figure 4:
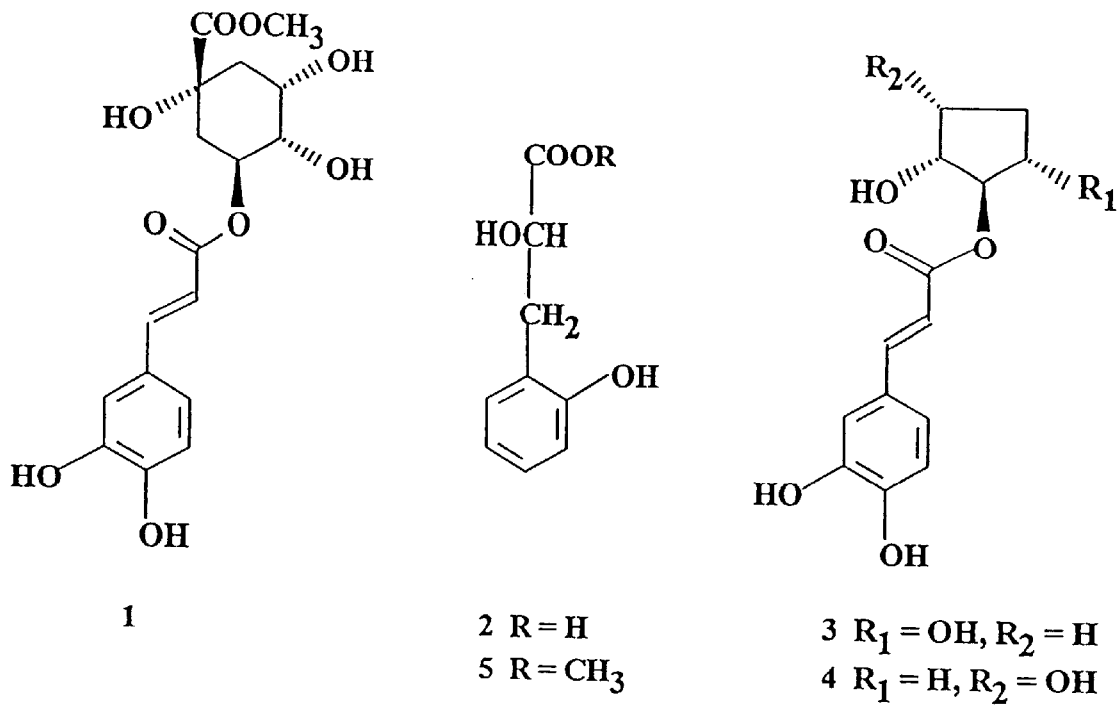
FIG. 4 shows selected phenolics isolated from tart cherries.

Other compounds isolated from the ethyl acetate extract of cherry fruits and characterized by spectral methods include: 1-(3'-methoxy,4'-hydroxy cinnamoyl) quinic acid, 2-hydroxy-3-(2'-hydroxyphenyl) propanoic acid, methyl 2-hydroxy-3-(2'-hydroxyphenyl) propanoate, D(+)-malic acid, β-sitosterol and β-sitosterol glucoside. FIG. 4 shows some of the phenolics that were isolated. The anthocyanin components obtained from the juice fraction also have been identified and fully characterized (Chandra, A., et al., J. Agric. Food Chem. 41:1062 (1993); Wang, H. et al., J. Agric. Food Chem. 45:2556–2560 (1997)); the results indicate that these compounds contain potent antioxidant activity.

As shown in FIG. 4, the compound

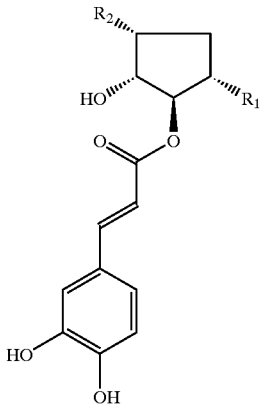

may exist as an isomer or in the pure form where $R_1$ and $R_2$ are selected from the group consisting of a hydroxyl and a hydrogen and one of the $R_1$ and $R_2$ is the hydroxyl. The compound may be the isomer of the above compound wherein $R_1$ is hydroxyl and $R_2$ is hydrogen. This particular isomer of the compound is 1-(3',4'-dihydroxycinnamoyl)-cyclopenta-2,5-diol, which is isolatable as a pure compound from tart cherries. The compound may also be the isomer of the above compound wherein $R_1$ is hydrogen and $R_2$ is hydroxyl. This particular isomer of the compound is 1-(3', 4'-dihydroxycinnamoyl)-cyclopenta-2,3-diol, which is isolatable as a pure compound from tart cherries.

EXAMPLES 1 TO 5

The following Examples show that tart cherry anthocyanins, cyanidin, or cherry fruits inhibit intestinal tumorigenesis in Min mice. Forty-eight Min mice were randomly assigned to five treatment groups at 4–5 weeks of age and fed treatment diets for 10 weeks. The treatments were:

1) Modified AIN-93G control diet, 2) The control diet +800 ppm anthocyanins in drinking water, 3) The control diet+200 ppm cyanidin in drinking water, 4) The control diet+200 ppm sulindac in drinking water, 5) Modified control diet containing 20% freeze dried pitted tart cherries. Only mean diameter, not the number of adenomas in the small intestine was reduced by sulindac, whereas diameter was increased by cherry diet (p<0.05). Mice consuming cherry diet, anthocyanins, or cyanidin had significantly fewer cecal adenomas than the controls, whereas mice consuming sulindac had significantly more cecal adenomas than controls. Mice treated with sulindac had the greatest number of colonic adenomas (p<0.05). Colon tumor volume was not significantly influenced by treatment. Sulindac inhibits small intestinal tumorigenesis and anthocyanins and cyanidin inhibit cecal tumorigenesis. This suggests that they may have different target sites in the intestine for exerting their antitumorigenic actions in Min mice.

Methods

All research was conducted with approval of the Michigan State University, East Lansing, Mich., All-University Committee on animal use and care. Mice were housed in MSU Laboratory, Animal Resources maintained facilities. A colony of Min mice was maintained by crossing male Min mice ($Apc^{min}/Apc^+$) with normal adult C57BL/6J female mice. Mice were housed in a temperature and humidity-controlled room (20–22° C., 70%) with a 12-h light/dark cycle. At three weeks of age, mice were bled from the dorsal pedal vein (30 $\mu$L) for genotyping analysis to identify $Apc^{min}/Apc^+$ using polymerase chain reaction (PCR) analysis and subsequent gel electrophoresis analysis. Forty-eight Min mice identified were randomly assigned to five treatment groups (7 to 11 per treatment) at 4 or 5 weeks of age and fed treatment diets for 10 weeks. The treatments were:

1) Modified AIN-93G control diet and 50 ppm ascorbic acid in drinking water (n=11)
2) The control diet+50 ppm ascorbic acid and 800 ppm anthocyanins in drinking water (n=9)
3) The control diet+50 ppm ascorbic acid and 200 ppm cyanidin in drinking water (n=7)
4) The control diet+50 ppm ascorbic acid and 200 ppm sulindac in drinking water (n=10)
5) 20% freeze-dried cherries+50 ppm ascorbic acid in drinking water (n=11).

Ingredient composition of diets is in Table 1. All diets contained 22% protein, 15% fat (soybean oil) and 5% cellulose contents. Distilled water was used for drinking water. Ascorbic acid was added to provide low pH for keeping anthocyanins and cyanidin in solution since they are stable only under pH 7. The concentration of sulindac (200 ppm) was based on the effective range found from most studies that have shown sulindac to reduce intestinal neoplasia. Cyanidin concentration (200 ppm) was matched to that of sulindac. Anthocyanins was tested at the level four times the cyanidin concentration because anthocyanins are the glycosylated cyanidin and the level (800 ppm) has equivalent amount of flavylium cation. Red tart pitted cherries (Peerson Farms, Inc., Shelby, Mich.) were frozen, freeze-dried, ground using plate grinder, and then screened to pass a 1 mm screen before they were incorporated into the diet at the expense of sucrose, cornstarch and dyetrose. One hundred grams of the experimental diet included 23 g of ground cherries to make 20% of cherries in the diet because dry matter of cherries was 75%, whereas that of AIN-93G diet was 91%.

Body weight was measured once a week until mice were sacrificed at the end of treatment period. Upon sacrifice by carbon dioxide asphyxiation, the liver was removed and frozen immediately for confirmatory PCR analysis. The entire small intestine, cecum, and colon were removed from each mouse to determine the number and size of adenomas. The tissues were separated into the following sections: proximal one-third of small intestine, middle one-third of small intestine, distal one-third of small intestine, cecum, and colon. All intestinal sections were opened longitudinally, rinsed thoroughly with water, fixed overnight in 10% neutral-buffered formalin, and then stained with 0.2% methylene blue. Tumor number and size (diameter for flat tumors or volume in the case of three-dimensional tumors) were determined in each intestinal segment on 1 mm grid transparency by direct counting with the aid of a dissecting microscope. Tumor numbers in each small intestinal segment were summed to obtain a total small intestine tumor burden for each mouse.

Tumor number and tumor diameter in the small intestine were analyzed by one-way analysis of variance to detect the effects of treatments. For tumor numbers and volume in cecum and colon, data were transformed to ranks and then analyzed by one-way analysis of variance. When significant treatment effects were detected (P<0.05), means were compared using the Least Significant Difference method.

TABLE 1

Composition of the experimental diets (Percentage of diet)

| Ingredient | Modified AIN-93G diet | 20% Cherries diet |
| --- | --- | --- |
| Casein | 22.12 | 22.12 |
| Soybean Oil | 15.00 | 15.00 |
| Corn Starch | 31.72 | 24.22 |
| DEXTROSE | 10.57 | 8.07 |
| Sucrose | 10.00 | 0.00 |
| AIN-93G-MX | 3.87 | 3.87 |
| AIN-93G-VX | 1.11 | 1.11 |
| L-Cystine | 0.33 | 0.33 |
| Choline Bitartrate | 0.28 | 0.28 |
| Tert-Butylhydroquinone | 0.003 | 0.003 |
| Cellulose | 5.00 | 5.00 |
| Freeze-Dried Cherries | 0.00 | 20.00 |

Results and Discussion

There are no differences found in numbers of adenomas in the small intestine and in the three sections of the small intestine (Table 2). There was a trend that sulindac in drinking water and 20% cherry diet reduced the number of adenoma in the proximal section of the small intestine (P=0.05). These findings are contradicted by the results from many studies which showed significant reduction of intestinal tumor multiplicity by sulindac in Min mice (Mahmoud, N. N., et al, Carcinogenesis 19:87–91 (1998); Chiu, C.-H., et al, Cancer Res. 57:4267–4273 (1997)). Small number of mice per treatment group (7 to 11) and wide range of intrastrain variations on adenoma development may account for these contradictory results. However, mean diameter of adenoma in the small intestine was significantly reduced by sulindac compared to control diet whereas it was increased by cherry diet (Table 3). Neither anthocyanins nor cyanidin in drinking water affected the number and size of the small intestinal adenomas.

TABLE 2

Adenoma numbers in the small intestine

| Treatment | Total | Proximal | Middle | Distal |
|---|---|---|---|---|
| AIN93G Control | 45.9 ± 12.6 | 11.1 ± 2.8 | 15.5 ± 4.7 | 19.3 ± 6.2 |
| Anthocyanins | 67.3 ± 13.9 | 17.0 ± 3.1 | 23.4 ± 5.1 | 26.8 ± 6.8 |
| Cyanidin | 51.3 ± 15.8 | 15.6 ± 3.5 | 15.7 ± 5.8 | 20.0 ± 7.8 |
| Sulindac | 24.7 ± 13.2 | 5.6 ± 2.9 | 9.1 ± 4.9 | 10.0 ± 6.5 |
| Cherries | 37.8 ± 12.6 | 7.8 ± 2.8 | 12.6 ± 4.7 | 17.4 ± 6.2 |

Each value represents mean ± SEM

TABLE 3

Adenoma diameters in the small intestine

| Treatment | Total Adenoma Diameter (mm) | Mean Adenoma Diameter (mm) |
|---|---|---|
| AIN93G Control | 65.3 ± 17.6 | 1.39 ± 0.10$^b$ |
| Anthocyanins | 90.9 ± 19.4 | 1.34 ± 0.10$^b$ |
| Cyanidin | 67.4 ± 22.0 | 1.25 ± 0.11$^b$ |
| Sulindac | 23.5 ± 18.4 | 0.93 ± 0.10$^a$ |
| Cherries | 67.7 ± 17.6 | 1.66 ± 0.09$^c$ |

Each value represents mean ± SEM
Different superscripts indicate significant differences (P < 0.05)

Mice consuming 20% tart cherry diet had less adenomas in the cecum and so did those consuming anthocyanins and cyanidins. In contrast, mice consuming sulindac had a significantly higher number of cecal adenomas. A similar trend was found in the number of adenomas in the colon; cherry and anthocyanin consuming mice had adenomas than mice consuming sulindac. Sulindac consuming mice had twice as many adenomas as those of mice in cherry diet (P<0.05). The size of adenoma in the cecum is determined by their volume. Cherries, anthocyanins and cyanidin reduced, while sulindac increased, the size of adenomas. Cherry was intermediate in efficacy of reduction of the adenoma diameter. No differences were found in the size of the colonic adenomas determined by the three-dimensional volume of adenomas.

TABLE 4

Adenoma numbers and volume in the cecum and colon

| Treatment | Cecum Number | Cecal Total Volume (mm$^3$) | Colon Number | Colon Total Volume (mm$^3$) |
|---|---|---|---|---|
| AIN93G Control | 1.91 ± 0.50$^a$ | 2.50 ± 0.77$^a$ | 3.00 ± 0.64$^{ab}$ | 1.95 ± 1.79 |
| Antho-cyanins | 0.56 ± 0.56$^b$ | 0.67 ± 0.85$^b$ | 2.78 ± 0.71$^a$ | 3.52 ± 1.98 |
| Cyanidin | 0.57 ± 0.63$^b$ | 0.56 ± 0.96$^b$ | 3.71 ± 0.80$^{ab}$ | 3.51 ± 2.24 |
| Sulindac | 4.00 ± 0.53$^c$ | 4.00 ± 0.81$^a$ | 5.30 ± 0.67$^b$ | 3.35 ± 1.88 |
| Cherries | 0.54 ± 0.50$^b$ | 1.63 ± 0.77$^b$ | 2.36 ± 0.64$^a$ | 7.58 ± 1.79 |

Each value represents mean ± SEM
Different superscripts indicate significant differences (P < 0.05)

Solid tumor numbers cecum and colon were determined (tumor was three-dimensional and visibly raised towards the lumenal side of the tissue). There were no differences detected in the average number of solid tumors in the cecum and colon even though anthocyanins and cyanidin treatments numerically reduced the average number (Table 5). In summary, feeding of tart cherry diet (20%) seemed to suppress adenoma multiplicity in cecum and in colon, to a lesser extent. However, feeding cherries enhanced the growth of adenoma in the small intestine by increasing the diameter of adenoma. In the case of sulindac, feeding via drinking water, it significantly reduced the size of adenomas in small intestine but increased the number of adenomas in cecum and colon in Min mice. The chemopreventive effects of anthocyanins, cyanidin and cherry diet and sulindac were not consistent through the intestinal tract suggesting that they may have different target sites in the intestine for exerting their antitumorigenic actions on the development of intestinal neoplasia in Min mice.

TABLE 5

Average number of solid tumors in cecum and colon

| Treatment | Cecum | Colon | Total |
|---|---|---|---|
| AIN93G Control | 0.27 ± 0.11 | 0.27 ± 0.17 | 0.55 ± 0.20 |
| Anthocyanins | 0.00 ± 0.11 | 0.22 ± 0.18 | 0.22 ± 0.22 |
| Cyanidin | 0.00 ± 0.13 | 0.14 ± 0.21 | 0.14 ± 0.25 |
| Sulindac | 0.20 ± 0.11 | 0.20 ± 0.17 | 0.40 ± 0.21 |
| Cherries | 0.18 ± 0.11 | 0.45 ± 0.17 | 0.64 ± 0.20 |

Each value represents mean ± SEM

It is intended that the foregoing description be only illustrative of the present invention and that the present invention be limited only by the hereinafter appended claims.

We claim:

1. A method for suppressing adenoma multiplicity in a mammal with a mutation in an adenomatous polyposis coli (APC) gene which comprises:
   providing a composition comprising a anthocyanin or cyanidin and administering the composition to the mammal in an amount and over a period of time sufficient to suppress the adenoma multiplicity in the mammal.

2. The method of claim 1 wherein the composition is administered to the mammal by feeding, topical application or injection.

3. The method of claim 1 wherein the composition consists essentially of one or more of the anthocyanin.

4. The method of claim 1 wherein the composition comprises cyanidin.

5. The method of claim 1 wherein the composition comprises an anthocyanin.

6. A method for suppressing adenoma multiplicity and volume in the cecum of a mammal with a mutation in an adenomatous polyposis coli (APC) gene which comprises:

feeding the mammal a composition comprising an anthocyanin or cyanidin derived from a berry in an amount and over a period of time sufficient to suppress the adenoma multiplicity and volume in the cecum of the mammal.

7. The method of claim 6 wherein the berry is a cherry.

8. The method of claim 6 composition comprises isolated anthocyanins.

9. The method of claim 6 wherein the mammal is human.

10. The method of claim 6 wherein the composition comprises cyanidin.

11. The method of claim 6 wherein the composition comprises an anthocyanin.

12. The method of any one of claims 6, 7, 8, or 9 wherein the amount is between 0.1 to 300 mg per day per kg body weight of the mammal.

13. A method for treating intestinal adenomas a mammal with a mutation in an adenomatous polyposis coli (APC) gene which causes intestinal adenomas in the cecum in a mammal which comprises:

(a) feeding the mammal a composition comprising an anthocyanin or cyanidin derived from cherries with malic acids and sugars removed in an amount and over a period of time sufficient to treat the mammal.

14. The method of claim 13 wherein the composition comprises isolated anthocyanins.

15. The method of claim 13 wherein the mammal is human.

16. The method of claim 13 wherein the mammal is a mouse.

17. The method of claim 13 wherein the composition consists essentially of one or more of the anthocyanins.

18. The method of claim 13 wherein the composition comprises cyanidin.

19. The method of claim 13 wherein the composition comprises an anthocyanin.

20. The method of any one of claims 8, 10 or 11 wherein the amount is between about 0.1 to 300 mg per day per kg of body weight of the mammal.

21. A method for inhibiting the number and volume of human colon cancer tumor cells resulting from a mutation of an adenomatous polyposis coli (APC) gene in a the mammal which comprises:

feeding the mammal a composition derived from a berry with malic acid and sugars removed and contacting said composition to the tumor comprising an anthocyanin selected from the group consisting of cyanidin-3-rutinoside, peonidin-3-rutinoside, cyanidin-3-sophoroside, cyanidin-3-xylosylrutinoside, cyanidin-3-gentiobioside, cyanidin-3-glucosylrutinoside and mixtures thereof, in an amount and over a period of time sufficient to allow the anthocyanin to inhibit the tumor cells.

22. A method for inhibiting the number and volume of human colon cancer tumor cells resulting from a mutation of an adenomatous polyposis coli (APC) gene which comprises:

providing a composition derived from a berry with malic acid and sugars removed and contacting said composition to the tumor comprising an anthocyanin selected from the group consisting of cyanidin-3-rutinoside, peonidin-3-rutinoside, cyanidin-3-sophoroside, cyanidin-3-xylosylrutinoside, cyanidin-3-gentiobioside, cyanidin-3-glucosylrutinoside and mixtures thereof, in contact with the tumor over a period of time sufficient to allow the anthocyanin to inhibit the tumor cells.

23. A method for inhibiting the number and volume of human colon cancer tumor cells resulting from a mutation of an adenomatous polyposis coli (APC) gene intestinal adenomas in the cecum in a mammal which comprises:

(a) feeding the mammal a composition comprising an anthocyanin selected from the group consisting of cyanidin-3-rutinoside, peonidin-3-rutinoside, cyanidin-3-sophoroside, cyanidin-3-xylosylrutinoside, cyanidin-3-gentiobioside, cyanidin-3-glucosylrutinoside and mixtures thereof, from cherries with malic acid and sugars removed and contacting said composition to the tumor so that the composition comes in contact with the adenomas in an amount and over a period of time sufficient to allow the anthocyanin to inhibit the intestinal adenomas in the cecum.

\* \* \* \* \*

UNITED STATES PATENT AND TRADEMARK OFFICE
CERTIFICATE OF CORRECTION

PATENT NO.    : 6,656,914 B2
DATED         : December 2, 2003
INVENTOR(S)   : Muraleedharan G. Nair et al.

It is certified that error appears in the above-identified patent and that said Letters Patent is hereby corrected as shown below:

<u>Column 1,</u>
Lines 7 and 8, "Ser. No. 09/494,077, filed Jan. 23, 2000," should be -- Ser. No. 09/494,077, filed Jan. 28, 2000, --.

<u>Column 11,</u>
Line 27, "malic acids and" should be -- malic acid and --.
Line 40, "claims 8, 10 or 11" should be -- claims 13, 14 or 15 --.

Signed and Sealed this

Sixth Day of April, 2004

JON W. DUDAS
*Acting Director of the United States Patent and Trademark Office*